US010667732B2

(12) United States Patent
Umasankar et al.

(10) Patent No.: US 10,667,732 B2
(45) Date of Patent: Jun. 2, 2020

(54) METHOD FOR TRANSDERMAL MEASUREMENT OF VOLATILE ANESTHETICS

(71) Applicants: Yogeswaran Umasankar, Miami, FL (US); Shekhar Bhansali, Weston, FL (US); Ernesto A. Pretto, Jr., Miami, FL (US)

(72) Inventors: Yogeswaran Umasankar, Miami, FL (US); Shekhar Bhansali, Weston, FL (US); Ernesto A. Pretto, Jr., Miami, FL (US)

(73) Assignees: The Florida International University Board of Trustees, Miami, FL (US); University of Miami, Miami, FL (US)

( * ) Notice: Subject to any disclaimer, the term of this patent is extended or adjusted under 35 U.S.C. 154(b) by 105 days.

(21) Appl. No.: 15/593,587

(22) Filed: May 12, 2017

(65) Prior Publication Data

US 2018/0325429 A1    Nov. 15, 2018

(51) Int. Cl.
*A61B 5/05* (2006.01)
*A61B 5/1477* (2006.01)
*G01N 27/407* (2006.01)
*A61B 5/145* (2006.01)
*A61B 10/00* (2006.01)
(Continued)

(52) U.S. Cl.
CPC ........ *A61B 5/1477* (2013.01); *A61B 5/14517* (2013.01); *A61B 10/0064* (2013.01); *G01N 27/4074* (2013.01); *G01N 33/0049* (2013.01); *G01N 33/948* (2013.01); *A61B 5/14532* (2013.01); *A61B 5/14542* (2013.01); *A61B 5/14546* (2013.01); *A61B 5/681* (2013.01); *A61B 5/6804* (2013.01); *A61B 5/6807* (2013.01); *H01M 2008/1095* (2013.01)

(58) Field of Classification Search
CPC .................................................. A61B 5/14517
See application file for complete search history.

(56) References Cited

U.S. PATENT DOCUMENTS 5,133,857 A * 7/1992 Alberti ............... G01N 27/4073
                                                        204/412
5,220,919 A * 6/1993 Phillips ............... G01N 33/4972
                                                        128/903
(Continued)

FOREIGN PATENT DOCUMENTS

WO    WO 2016044711 A1 *  3/2016  ....... G01N 33/48707

OTHER PUBLICATIONS

Najafi et al, Electrochemical Homogenous Catalysis of the Isoflurane Reduction in Presence of Iron(III) Tetraphenylporphyrin Chloride, 2013, J. Braz. Chem. Soc., 24(10): 1679-1684.*
(Continued)

*Primary Examiner* — Eric J Messersmith
(74) *Attorney, Agent, or Firm* — Saliwanchik, Lloyd & Eisenschenk (57) ABSTRACT

Devices and methods of making and using the device for the non-invasive detection of volatile anesthetics are provided. The devices are capable of measuring the concentration of volatile anesthetics transdermally and in a non-invasive manner. The devices and methods can be applied in detection of volatile anesthetics in samples collected from human skin perspiration.

15 Claims, 4 Drawing Sheets

Lateral view (51) Int. Cl.
  G01N 33/94 (2006.01)
  G01N 33/00 (2006.01)
  *A61B 5/00* (2006.01)
  *H01M 8/1018* (2016.01)

(56) References Cited

U.S. PATENT DOCUMENTS

| | | | | |
|---|---|---|---|---|
| 5,298,146 | A * | 3/1994 | Braden | G01N 33/0031 204/406 |
| 5,667,652 | A * | 9/1997 | Liu | G01N 27/4074 204/412 |
| 6,144,869 | A * | 11/2000 | Berner | A61B 5/14532 600/309 |
| 6,299,757 | B1 * | 10/2001 | Feldman | C12Q 1/001 205/775 |
| 7,258,773 | B2 * | 8/2007 | Zhou | G01N 27/4073 204/426 |
| 2002/0026110 | A1 * | 2/2002 | Parris | A61B 5/14532 600/347 |
| 2002/0187075 | A1 * | 12/2002 | Nadanami | G01N 27/4074 422/98 |
| 2005/0251088 | A1 * | 11/2005 | Kwon | A61K 9/0021 604/60 |
| 2007/0114128 | A1 * | 5/2007 | Lau | G01N 27/3335 204/284 |
| 2007/0299617 | A1 * | 12/2007 | Willis | A61B 5/14532 702/19 |
| 2008/0156661 | A1 * | 7/2008 | Cooper | A61B 5/14532 205/775 |
| 2011/0000797 | A1 * | 1/2011 | Henry | G01N 27/4168 205/780 |
| 2016/0338626 | A1 * | 11/2016 | Wang | A61C 19/04 |

OTHER PUBLICATIONS

Beckley et al, Volatile Solvents as Drugs of Abuse: Focus on the Cortico-Mesolimbic Circuitry, 2013, 38(13): 2555-2567.*
Jimenez et al, Interpretation of open circuit potential of two titanium alloys for a long time immersion in physiological fluid, 2009, Bulletin of the Transilvania University of Brasov, 2(51): 197-204.*
Jalal, et al. Multimodal technique to eliminate humidity interference for specific detection of ethanol. Biosensors and Bioelectronics. 87 (2017) p. 522-530 (published Aug. 30, 2016) (Year: 2016).*
Umasankar, et al. Wearable alcohol monitoring device with auto-calibration ability for high chemical specificity. 2016 IEEE 13th International Conference on Wearable and Implantable Body Sensor Networks (BSN). Jun. 14-17, 2016. pp. 353-358. (Year: 2016).*
A. A. Kulikovsky and P. Berg. Positioning of a Reference Electrode in a PEM Fuel Cell. Journal of the Electrochemical Society. 162(8) F843-F848 (2015) (Year: 2015).*
Jalal, et al. Development and Characterization of Fuel Cell Sensor for Potential Transdermal Ethanol Sensing. ECS Transactions 2016. 72(31) 25-31. (Year: 2016).*
Sanford et al., "Determination of ethanol in alcohol samples using a modular raman spectrometer," Journal of Chemical Education, Sep. 2001, pp. 1221-1225, vol. 78, No. 9.
Shabaneh et al., "Reflectance response of tapered optical fiber coated with graphene oxide nanostructured thin film for aqueous ethanol sensing," Optics Communications, Jul. 2, 2014, pp. 320-324, vol. 331.
Kadir et al., "Nb2O5 schottky based ethanol vapour sensors: effect of metallic catalysts," Sensors and Actuators B: Chemical, May 14, 2014, pp. 74-82, vol. 202.
Jiang et al., "Development of air-breathing direct ethanol fuel cells with PtSn as anode," Preprints of Papers—American Chemical Society, Division of Fuel Chemistry, 2004, pp. 668-670, vol. 49, No. 2.
Anderson et al., "The kinetics of transdermal ethanol exchange," Journal of Applied Physiology, Feb. 2006, pp. 649-655, vol. 100.
Izquierdo et al., "Imaging local surface reactivity on stainless steels 304 and 316 in acid chloride solution using scanning electrochemical microscopy and the scanning vibrating electrode technique," Electrochimica Acta, May 4, 2014, pp. 167-175, vol. 134.
An et al., "Synthesis and characterization of an ester-terminated organic semiconductor for ethanol vapor detection," Organic Electronics, Oct. 2014, pp. 2277-2284, vol. 15, No. 10.
Yu et al., "Performance evaluation of ZnO—CuO hetero junction solid state room temperature ethanol sensor," Materials Research Bulletin, Jul. 2012, pp. 1713-1718, vol. 47, No. 7.
Kim et al., "Highly sensitive and selective gas sensors using p-type oxide semiconductors: overview," Sensors and Actuators B: Chemical, Mar. 2014, pp. 607-627, vol. 192.
Jeng et al., "A versatile electrochemical fuel sensor for direct membrane fuel cell applications," Sensors and Actuators B: Chemical, Jul. 2007, pp. 278-283, vol. 125.
Kim et al., "Detection of ethanol gas concentration by fuel cell sensors fabricated using a solid polymer electrolyte," Sensors and Actuators B: Chemical, Aug. 2000, pp. 194-198, vol. 67.

* cited by examiner

Top view

FIG. 1A

Lateral view

FIG. 1B

Dorsal view

METHOD FOR TRANSDERMAL MEASUREMENT OF VOLATILE ANESTHETICS

BACKGROUND OF INVENTION

Volatile anesthetics are a family of halogenated ethers that can quickly evaporate and thereby be inhaled by patients in need of such treatment. The effects of anesthesia primarily depend upon the concentration of anesthetics administered at the site of action. Most volatile anesthetics are administered in gaseous form to patients via a closed or open breathing circuit involving, for example, an anesthetic mask, a laryngeal mask airway, or an endotracheal tube. The effectiveness of volatile anesthetics delivered via methods described above cannot be directly evaluated in the brain of a patient; instead, other methods that include, for example, measuring the concentration transdermally, must be employed.

Currently-available technologies for measuring transdermal content of volatile anesthetics have been limited to laboratory setups, which can be complex and non-transferrable to portable devices for clinical uses. Furthermore, these methods lack stability and consistency in detection results and lack the capability to accommodate continuous measurements.

As a result, there still remains a need for stable, selective, and portable sensors that are effective in evaluating volatile anesthetics in patients administered with the same.

BRIEF SUMMARY

Embodiments of the subject invention provide devices, and methods of making and using the same, for the non-invasive detection of volatile anesthetics.

Advantageously, the electrochemical sensors provided herein are highly stable and accurate, and applicable for low-cost, continuous monitoring of volatile anesthetics in transdermal perspiration samples.

In an embodiment, a fuel-cell based electrochemical detector can be capable of measuring (and/or configured to measure) the concentration of volatile anesthetics transdermally and in a non-invasive manner. The detector can comprise a sensor unit comprising a working electrode as an anode, a counter electrode as a cathode, a reference electrode, and a polymer electrolyte membrane, as well as circuitry capable of controlling (and/or configured to control) the potential applied to the sensor unit and circuitry capable of measuring (and/or configured to measure) the current output of the sensor unit.

In some embodiments, the fuel-cell based device can detect volatile anesthetics including, for example, isoflurane, sevoflurane, and desflurane.

In preferred embodiments, devices and methods provided herein can be applied in detection of volatile anesthetics in samples collected from human skin perspiration.

In a specific embodiment, the electrodes can comprise a material selected from iron, gold, nickel, platinum, carbon, and combinations thereof as a catalyst. Preferably, the catalyst can be deposited on the surface of the anode as a coating.

In another embodiment, a method of detecting the concentration of volatile anesthetics in a skin perspiration sample collected from a human subject can comprise: contacting a sample with the sensing device provided herein; obtaining open-circuit potential (OCP) of the sensor unit by scanning a range of voltage; comparing the OCP to a threshold value characteristic to the material employed in the working electrode; applying the OCP across the working and the reference electrodes while conducting a series of amperometric measurements; and determining the concentration of the volatile anesthetic based on the amperometric measurements.

In some embodiments, the device can be placed in direct contact with the skin surface of the subject.

Advantageously, the electrochemical sensor provided herein can be integrated into a wearable device for convenient and accurate detection of concentration of volatile anesthetics.

DETAILED DISCLOSURE

Embodiments of the subject invention provide devices, and methods of making and using the same, for the non-invasive detection of volatile anesthetics. In some embodiments, a fuel-cell based electrochemical detector of the subject invention is capable of measuring the concentration of volatile anesthetics transdermally and in a non-invasive manner.

In preferred embodiments, devices and methods provided herein can be applied in detection of volatile anesthetics in samples collected from human skin perspiration.

In an embodiment, a fuel cell based device can continuously detecting the concentration of volatile anesthetics in a sample, and the device can comprise:
- a sensor unit comprising a working electrode as an anode, a counter electrode as a cathode, a reference electrode, and a polymer electrolyte membrane, the anode and the cathode being separated by, and in electrical contact with, the electrolyte, the reference electrode being in electrical contact with the electrolyte and disposed adjacent to, though separated from, the counter electrode;
- circuitry capable of controlling the potential applied to the sensor unit; and
- circuitry capable of measuring the current output of the sensor unit.

In some embodiments, the electrolyte material can be a proton exchange membrane (PEM). In a preferred embodiment, the electrolyte is NAFION® (DuPont), a class of perfluorinated PEM. In an exemplary embodiment, the NAFION® membrane was a 424 reinforced with PTFE fiber measuring approximately 0.03 cm in thickness.

A PEM-based fuel cell operates with gaseous hydrogen as the fuel and oxygen from ambient air as the oxidant. In conventional PEM-based fuel cells, the PEM comprises one or more fluorinated polymers. It is desirable to employ PEMs with high proton conductivity at low relative humidity and long-term chemical, electrochemical, and thermal stability, as well as low gas permeability under normal operating conditions. In addition to NAFION®, other organic polymer membranes can also be used in the fuel cell based sensor as the electrolyte. Non-limiting examples include GORE-SELECT® reinforced membranes (W. L. Gore), ACIPLEX® (Asahi Chemicals), FLEMION® (Asahi Glass), and BAM® (Ballard Power) for cell operation temperature not exceeding 90° C.; other art-recognized sulfonated or phosphonated polymers can be used in high-temperature applications.

In some embodiments, the electrodes comprise stainless steel. In specific embodiments, the electrodes comprise micro-perforated stainless steel. At least one of the stainless steel electrodes (preferably, the anode) can be deposited with a thin, flexible coating of a material acting as a catalyst and a reaction mediator. In some embodiments, the coating material can include nickel, iron, gold, platinum, carbon, and combinations thereof. Those skilled in the art would recognize that other electrically conductive and semiconductive coating materials (or electrode materials) can also serve as catalyst for the redox reaction and accommodate electron transfer to generate electrochemical signals. In preferred embodiments, the coating comprises nickel. Advantageously, the fuel-cell based sensor constructed from stainless steel and nickel not only demonstrates efficacy in providing selective sensing capability for volatile anesthetics but also lowers the overall cost of the device.

A volatile anesthetic as used herein can be a pharmaceutical composition comprising, as the main component(s), at least one of the following compounds: isoflurane, sevoflurane, enflurane, and desflurane. In some embodiments, the volatile aesthetic can also be a gas such as, for example, nitrous oxide or xenon. In addition to volatile anesthetics, embodiments of the subject invention provide that the fuel-cell based sensor can be used to detect other volatile pharmaceutical compositions.

In certain embodiments, the volatile anesthetics that can be detected by the device provided herein have been previously administered to a human subject (e.g., a patient in need of anesthetic treatment) and transdermally diffused through the skin of the subject.

Figure 1A:
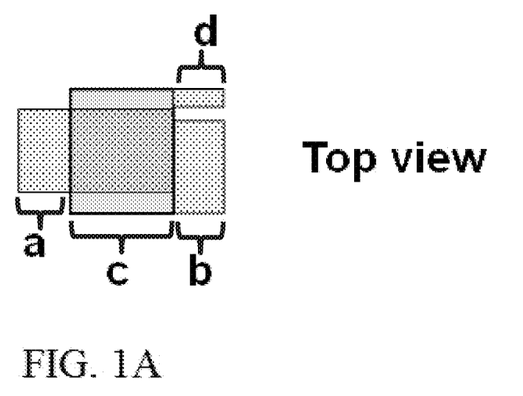
FIG. 1A is a top view of a preferred embodiment of the fuel-cell based sensor.
Figure 1B:
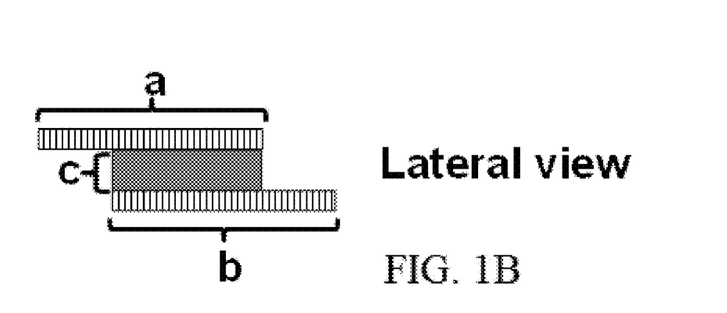
FIG. 1B is a lateral view of a preferred embodiment of the sensor.
Figure 1C:
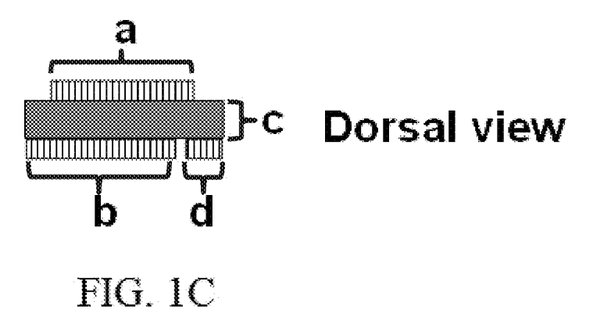
FIG. 1C is a dorsal view of a preferred embodiment of the sensor.

In some embodiments, the working electrode a is located on the anode side of the membrane c, and the counter electrode b and reference electrode d are placed on the cathode side of the membrane c (FIGS. 1A-1C). In an embodiment, the thickness of the micro-perforated stainless steel electrodes can be between about 0.01 cm and about 0.03 cm, and preferably about 0.02 cm. The active surface area of the working electrode a is preferably slightly less than that of the counter electrode b for the purpose of maximizing the extent of oxygen reduction at the counter electrode b and providing sufficient oxygen supply to consume the fuel at the working electrode/PEM interface. In an exemplary embodiment, the active surface area of the working electrode a can be about 1.2 cm² (e.g., 1.5 cm×0.8 cm), while that of the counter electrode b and the reference electrode d can be approximately 1.5 cm² (e.g., 1.5 cm×1.0 cm) and 0.3 cm² (e.g., 1.5 cm×0.2 cm), respectively.

In contrast to traditional fuel cells, which employ a two-electrode system (i.e., an anode and a cathode), an exemplary embodiment of the subject invention employs a three-electrode system. The three-electrode system is advantageous because, in a two-electrode system, the electrochemical potential measurement reflects the full-cell reaction potential, whereas in the three-electrode system the half-cell potential can be measured independently. In a three-electrode system, the current between the working electrode and the counter electrode is measured as a function of the applied potential between the two electrodes.

In the three-electrode system provided herein, the cathodic reaction can be represented by the following equations:

$$O_2 + e^- \rightleftharpoons O_2^{*-} \quad (1)$$

$$O_2^{*-} + R-X \rightarrow R-O_2^* + X^- \quad (2)$$

$$R-O_2^* + e^- \rightarrow R-O_2^- \quad (3)$$

where R is the volatile anesthetic compound, and X is a halogen molecule in the anesthetic compound. Subsequent to the reaction in Equation (3), oxygen is reduced at the cathode and the electrons are consumed in this process. Further, nickel deposited on the anode oxidizes in the presence of atmospheric oxygen, humidity, and applied potential, generating a current that flows towards the cathode. The current can then be detected using an amperometric method and quantified to delineate the concentration of the volatile anesthetics.

In some embodiments, the three-electrode system can be constructed in such a way that the working electrode a and the reference electrode d are located in close proximity to each other, albeit on opposite sides of the PEM electrolyte c, enabling easy exchange of H+ ions (FIGS. 1A and 1B). This design facilitates the monitoring of the anodic reaction of the fuel-cell based sensor.

One advantage of the three-electrode system is that it monitors only the anodic half-cell reaction as given in Equation (1). This can be achieved by measuring the potential between the anode and the reference electrode, and letting the current pass between the anode and the cathode. This mechanism yields a more stable signal of the concentration of the anesthetics at the anode than the traditional two-electrode system. Additional advantages of the three-electrode system includes, for example, a stable reference voltage provided by abundant atmospheric oxygen reduction occurring across the reference and working electrode, avoidance of short circuit voltage between the working and the reference electrode, and elimination of limited electron flow due to limited surface area of the counter electrode.

In some embodiments, the sample is a product of human transdermal diffusion process. Exemplary embodiments provide that the sample is obtained from human skin perspiration of a subject who has received anesthetics treatment.

In an embodiment, a method of continuously detecting the concentration of volatile anesthetics in skin perspiration collected from a human subject can comprise:
  contacting a sample with the sensing device provided herein;
  obtaining open-circuit potential (OCP) of the sensor unit by scanning a range of voltage;
  comparing the OCP to a threshold value characteristic to the material employed in the working electrode;

applying the OCP across the working and the reference electrode while conducting a series of amperometric measurements; and determining the concentration of the volatile anesthetic based on the amperometric measurements.

In some embodiments, the sensing device can be placed in direct contact with human skin. Human skin comprises epidermis and dermis as the outermost two layers. Volatile anesthetics diffused out of the epidermis interact with the anode of an exemplary fuel-cell based sensor when the sensor is disposed in close proximity to the skin surface.

In another embodiment, a device for determining the amount of volatile anesthetics in a skin perspiration sample collected from a human subject can comprise:

the fuel-cell based sensing device provided herein;

a means of displaying the concentration of the anesthetics measured with the sensing device;

circuitry capable of processing and analyzing the concentration data output by the sensing device; and optionally a casing that encloses the sensing device.

The anesthetics sensing device provided herein can be integrated with additional components for various applications. Embodiments of the integrated device include, but are not limited to, wrist watches, bracelets, and arm bands; apparel such as shirts, jackets, and pants; accessories such as gloves, glasses, goggles, necklaces, and lanyards; headsets and headbands; shoes; vehicle accessories such as a steering wheel and its cover, a transmission stick and its cover, ignition button, and keys.

In some embodiments, the measured anesthetics can be shown via a display capable of portraying data in the form of visual text and/or images. Non-limiting examples of the display include devices comprising liquid crystal materials, electrophoretic material, and/or electrochromic materials that are commonly found in applications such as electronic paper, computer monitors, handheld devices and the like.

In some embodiments, the fuel-cell based sensor provided herein can be incorporated (e.g., retrofitted) into devices manufactured by third parties.

Embodiments of the integrated devices comprise casings for the sensors provided herein and can help prevent circuitry damage and hold the sensor components together. The materials that can be used to develop the casings include, but are not limited to, polymers, fabrics, and metals.

In further embodiments, the integrated sensing device comprises an electronic platform for receiving user input.

In addition to monitoring the concentration of volatile anesthetics, technologies provided herein can also be used for sensors aimed to detect other chemical species capable of diffusing through the skin including, but not limited to, oxygen, carbon dioxide, carbon monoxide, acetone, glucose, salts, esters, aldehydes, and oxides of nitrogen.

Further, in some embodiments, the fuel-cell based sensor can be combined with other techniques including, but not limited to, ultrasound, electrotransport, and electroporation that facilitate the transport of volatile anesthetics through the skin, leading to minimal or no delay in estimating the concentration of the anesthetics based on the transdermal reading.

Advantageously, the fuel-cell based sensor provided herein can monitor the concentration of volatile anesthetics from skin perspiration and transdermal diffusion even in the presence of high humidity. This is accomplished by, in accordance with embodiments of the subject invention, taking advantage of low-cost materials such as stainless steel and nickel for the electrodes and the catalyst, respectively. This combination of devices and techniques allows selectivity in detecting transdermal content of volatile anesthetics and can be adapted in a variety of applications such as, for example, wearable devices.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

EXAMPLES

The following are examples that illustrate the aforementioned embodiments and should not be construed as limiting. All of the chemical supplies provided herein, unless otherwise noted, were obtained via commercial sources and are readily available for procurement.

Example 1—Coating an Electrode with a Catalyst for the Fuel-Cell Based Sensor

The coating of a catalyst (i.e., nickel) on the micro-perforated stainless steel sheet electrodes was achieved by a five-step process. The steps comprise: (i) anodically electrocleaning the stainless sheet for 5 mins with 25% $H_2SO_4$ below room temperature by applying a current density of 13.94 $A/m^2$. During electrocleaning, the stainless steel served as the anode and the lead sheet served as the cathode; (ii) acid-cleaning the stainless sheets at room temperature with 1:10:1000 solution of HCl, $H_2SO_4$, and DI water; (iii) Wood's nickel strike using 1.5M HCl and 1.009 M anhydrous nickel chloride solution and applying current densities of 4.65 $A/m^2$ and 1.4 $A/m^2$ for 2 mins each. In the Wood's nickel strike setup, a pure nickel sheet was used as the anode and the target electrode as the cathode; (iv) galvanostatically electroplating the sheets with nickel by Watt's deposition method at 50° C. at 0.2 A in a mixture of 0.93 M nickel sulfamate, 0.025 M nickel chloride, and 0.48 M boric acid solution; (v) baking and drying the sheets at 190° C. for 2 hrs. The voltage was maintained at below 3 V during the electroplating process. In some embodiments, a porous nickel sheet can be used as an electrode material in lieu of a nickel-coated micro-perforated stainless steel sheet.

Example 2—Measuring the Effect of Volatile Anesthetics on the OCP of the Sensor

Figure 2:
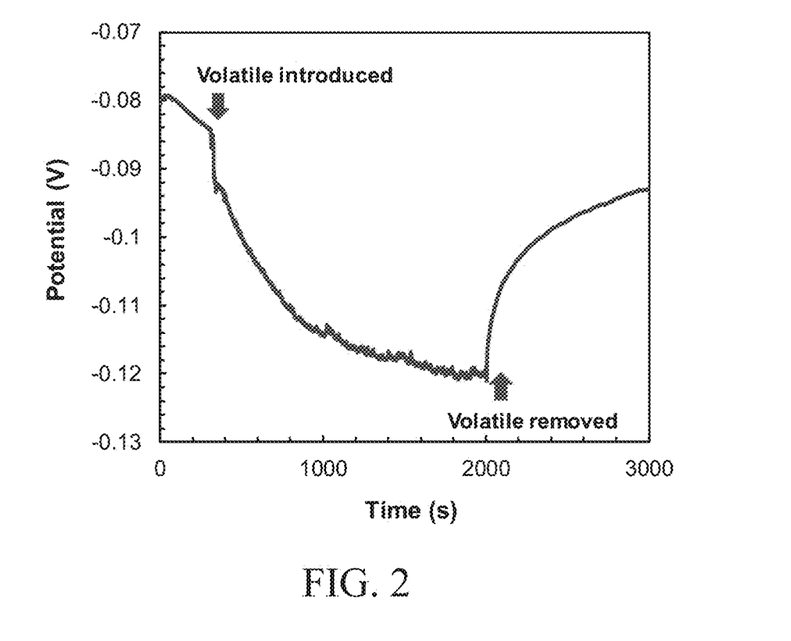
FIG. 2 shows the results of an open circuit potential study of the fuel-cell based sensor in the presence of isoflurane, an exemplary flurane composition.
Figure 3:
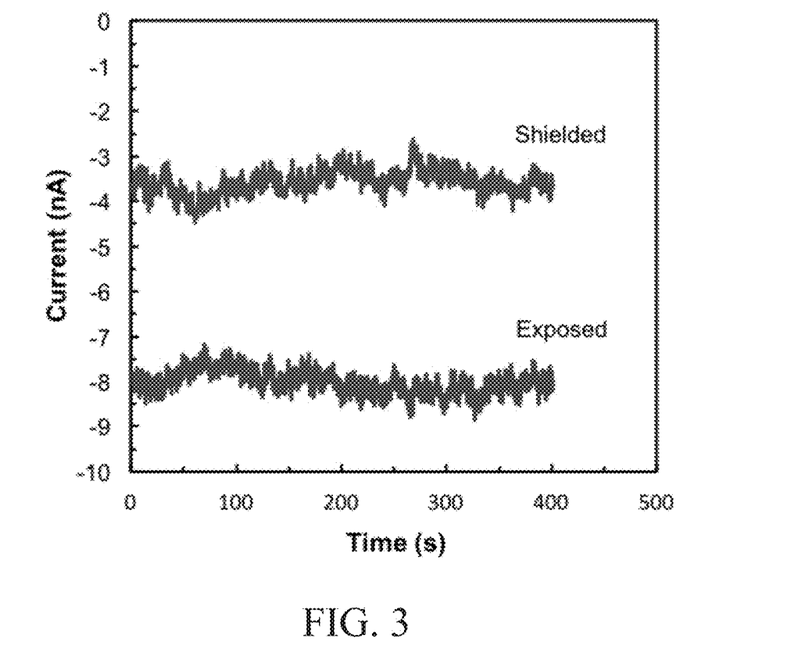
FIG. 3 shows the amperometric/current signals of the sensor in the presence ("Exposed") and absence ("Shielded") of isoflurane.

The open circuit potential (OCP) of the fuel-cell based sensor in the presence of isoflurane was examined and the results are as shown in FIG. 2. An isoflurane cloud was introduced to the sensor system after 500 s of OCP scanning. Amperometric studies were completed with the sensor exposed and shielded to isoflurane vapor (FIG. 3). The effect of isoflurane vapor concentration on the current measured by the senor was also investigated.

Figure 4:
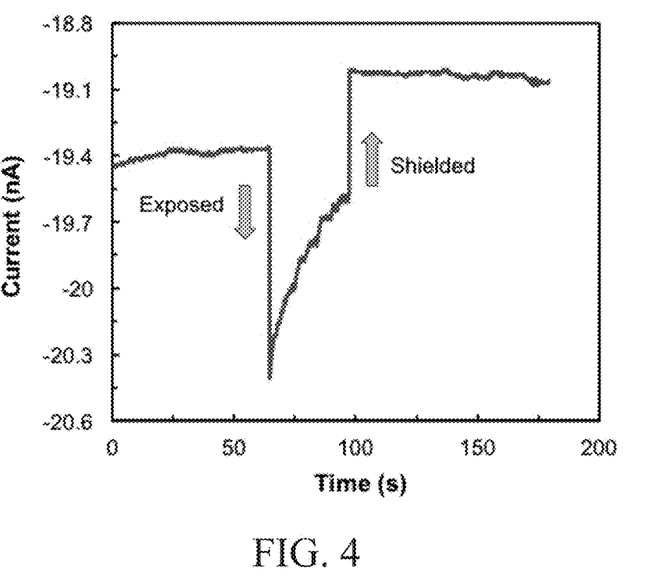
FIG. 4 shows changes in amperometric/current signals of the sensor when exposed to isoflurane and shielded from isoflurane.

As shown in FIG. 2, the OCP deviated 40 mV from the point of introducing the isoflurane cloud, indicating a potential difference was resulted due to the redox chemical reactions described herein. After removing the volatile cloud, the OCP signal of the sensor gradually reached a steady state (see also FIG. 4).

Figure 5:
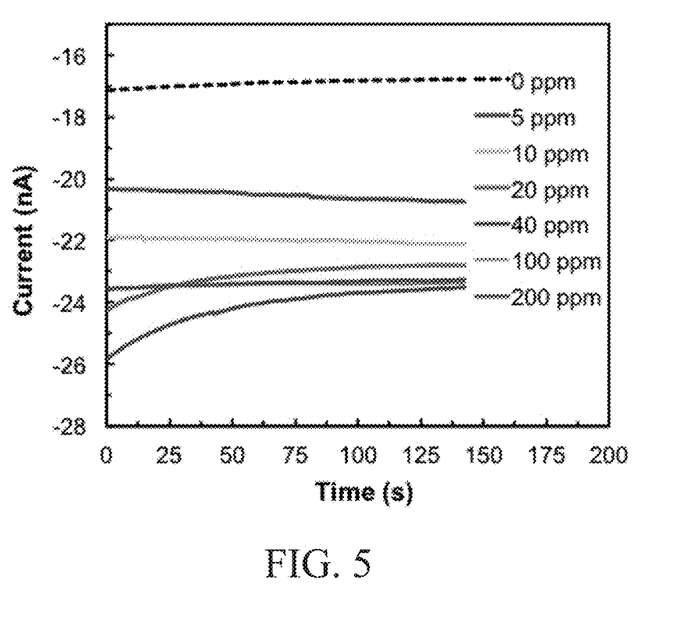
FIG. 5 shows the effect of isoflurane on the current measured by the sensor. The experiments were carried out with and without isoflurane (concentration range between 5 ppm and 200 ppm). Linear response with respect to the concentration occurred between 5 ppm and 40 ppm.
Figure 6:
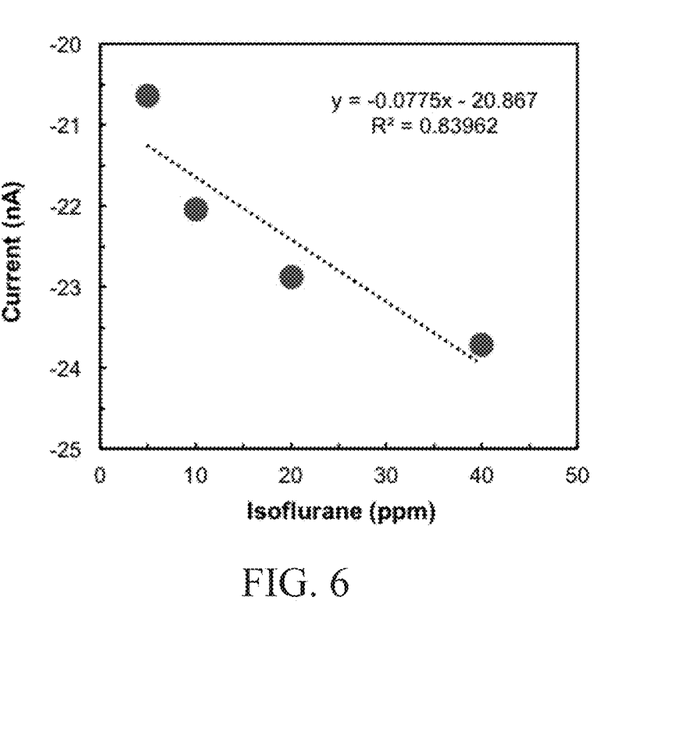
FIG. 6 shows the linear calibration fit obtained from the isoflurane amperometric studies. The linear response was from 5 ppm to 40 ppm with a slope of 77.5 pA.

The effect of concentration of isoflurane on the current measured by the sensor can be seen in FIG. 5. A linear response was observed when the concentration of the isoflurane was between 5 ppm and 40 ppm. This linear response was further analyzed using a calibration fit as shown in FIG. 6.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. C. L. Sanford, B. A. Mantooth, Determination of ethanol in alcohol samples using a modular raman spectrometer. *J. Chem. Educ.* 2001, 78, 1221-1224.
2. A. A. Shabaneh, S. H. Girei, P. T. Arasu, W. B. W. A. Rahman, A. A. A. Bakar, A. Z. Sadek, H. N. Lim, N. M. Huang, M. H. Yaaco, Reflectance response of tapered optical fiber coated with graphene oxide nanostructured thin film for aqueous ethanol sensing. *Optics Comm.* 2014, 331, 320-324.
3. T. K. An, H.-J. Yun, R. Narote, R. Kim, S. U. Lee, Y. Kim, S. Nam, H. Cha, Y. J. Jeong, K. Kim, S. Cho, S.-K. Kwon, Y.-H. Kim, C. E. Park, Synthesis and characterization of an ester-terminated organic semiconductor for ethanol vapor detection. *Org. Electronics* 2014, 15, 2277-2284.
4. Ming-Ru Yu, Gobalakrishnan Suyambrakasam, Ren-Jang Wu, Murthy Chavali, Performance evaluation of ZnO— CuO hetero junction solid state room temperature ethanol sensor. *Mat. Res. Bulletin* 2012, 47, 1713-1718.
5. R. A. Kadir, R. A. Rani, A. S. Zoolfakar, J. Z. Ou, M. Shafiei, W. Wlodarski, K. Kalantar-zadeh, Nb2O5 Schottky based ethanol vapour sensors: Effect of metallic catalysts. *Sens. Act. B: Chem.* 2014, 202, 74-82.
6. H.-J. Kim, J.-H. Lee, Highly sensitive and selective gas sensors using p-type oxide semiconductors: overview. *Sens. Act. B: Chem.* 2014, 192, 607-627.
7. K.-T. Jeng, W.-M. Huang, C.-C. Chien, N.-Y. Hsu, A versatile electrochemical fuel sensor for direct membrane fuel cell applications. *Sens. Act. B: Chem.* 2007, 125, 278-283.
8. L. Jiang, Z. Zhou, S. Wang, J. Liu, X. Zhao, G. Sun, Q. Xin, B. Zhou, Development of air-breathing direct ethanol fuel cells with PtSn as anode. *Prepr. Pap.-Am. Chem. Soc., Div. Fuel Chem.* 2004, 49, 668-670.
9. K.-C. Kim, S. M. Cho, H.-G. Choi, Detection of ethanol gas concentration by fuel cell sensors fabricated using a solid polymer electrolyte. *Sens. Act. B: Chem.* 2000, 67, 194-198.
10. J. C. Anderson, M. P. Hlastala, The kinetics of transdermal ethanol exchange. *J. Applied Physiology* 2006, 100, 649-655.
11. J. Izquierdo, L. Martín-Ruíz, B. M. Fernández-Pérez, L. Fernández-Mérida, J. J. Santana, R. M. Souto, Imaging local surface reactivity on stainless steels 304 and 316 in acid chloride solution using scanning electrochemical microscopy and the scanning vibrating electrode technique. *Electrochim. Acta* 2014, 134, 167-175.
12. W. B. Harding, "*Testing of Metallic and Inorganic Coatings*", ASTM International, pp. 327-328, 1987.

What is claimed is:

1. A fuel-cell based sensing device for continuously detecting a concentration of a volatile anesthetic in a sample, the sensing device comprising:
    a sensor unit comprising a working electrode as an anode, a counter electrode as a cathode, a reference electrode, and an electrolyte;
    circuitry configured to control a potential applied to the sensor unit; and
    circuitry configured to measure a current output between the working electrode and the counter electrode and a potential between the working electrode and the reference electrode through the electrolyte,
    the anode and the cathode being separated by, and in electrical contact with, the electrolyte,
    the working electrode being disposed on an anode side of the electrolyte,
    the counter electrode being disposed on a cathode side of the electrolyte opposite to the anode side of the electrolyte such that the counter electrode faces the working electrode,
    the reference electrode being disposed on the cathode side of the electrolyte,
    the reference electrode being in electrical contact with the electrolyte and disposed adjacent to, though separated from, the counter electrode,
    the sample being a product of a human transdermal diffusion process,
    a thickness of the electrolyte being in a range of from 0.01 cm to 0.03 cm such that $H^+$ ions exchange between the working electrode and the reference electrode,
    a first part of the anode side of the electrolyte corresponding to the counter electrode being uncovered by the working electrode and a second part of the anode side of the electrolyte corresponding to the reference electrode being uncovered by the working electrode,
    the working electrode having an extended portion physically separated from the electrolyte and extending away from the electrolyte in a first direction while maintaining a constant width of the working electrode, the counter electrode having an extended portion physically separated from the electrolyte and extending away from the electrolyte in a second direction opposite to the first direction while maintaining a constant width of the counter electrode, the reference electrode having an extended portion physically separated from the electrolyte and extending away from the electrolyte in the second direction while maintaining a constant width of the reference electrode, an active surface area of the reference electrode being smaller than an active surface area of the working electrode and an active surface area of the counter electrode, the working electrode, the counter electrode, and the reference electrode each comprising micro-perforated stainless steel, and the working electrode further comprising a coating of nickel.

2. The device according to claim 1, the electrolyte being a proton exchange membrane (PEM).

3. The device according to claim 1, an active surface area of the working electrode being smaller than an active surface area of the counter electrode.

4. The device according to claim 1, the sample comprising human skin perspiration.

5. The device according to claim 1, the counter electrode and the reference electrode each being coated with a catalytic material comprising nickel, gold, iron, platinum, carbon, or a combination thereof, the catalytic material acting as a reaction mediator.

6. The device according to claim 5, the counter electrode and the reference electrode each being coated with nickel.

7. The device according to claim 1, the volatile anesthetic being a hydrogenated ether selected from isoflurane, sevoflurane, enflurane, and desflurane.

8. A method of continuously detecting a concentration of a volatile anesthetic in a skin perspiration sample collected from a human subject, the method comprising:

contacting a sample of human skin perspiration with a fuel-cell based sensing device, the sensing device comprising:
a sensor unit comprising a working electrode as an anode, a counter electrode as a cathode, a reference electrode, and an electrolyte;
circuitry configured to control a potential applied to the sensor unit; and
circuitry configured to measure a current output between the working electrode and the counter electrode and a potential between the working electrode and the reference electrode through the electrolyte;
obtaining open-circuit potential (OCP) of the sensor unit by scanning a range of voltage;
comparing the OCP to a threshold value characteristic to a material employed in the working electrode;
applying the OCP across the working electrode and the reference electrode while conducting a series of amperometric measurements; and
determining the concentration of the volatile anesthetic based on the amperometric measurements,
the anode and the cathode being separated by, and in electrical contact with, the electrolyte,
the working electrode being disposed on an anode side of the electrolyte,
the counter electrode being disposed on a cathode side of the electrolyte opposite to the anode side of the electrolyte such that the counter electrode faces the working electrode,
the reference electrode being disposed on the cathode side of the electrolyte,
the reference electrode being in electrical contact with the electrolyte and disposed adjacent to, though separated from, the counter electrode,
the working electrode, the counter electrode, and the reference electrode each comprising a thin coating of a material comprising nickel, iron, gold, platinum, carbon, or a combination thereof, as a catalyst,
the sample of human skin perspiration being collected from a subject treated with anesthetics,
a thickness of the electrolyte being in a range of from 0.01 cm to 0.03 cm such that $H^+$ ions exchange between the working electrode and the reference electrode,
a first part of the anode side of the electrolyte corresponding to the counter electrode being uncovered by the working electrode and a second part of the anode side of the electrolyte corresponding to the reference electrode being uncovered by the working electrode,
the working electrode having an extended portion physically separated from the electrolyte and extending away from the electrolyte in a first direction while maintaining a constant width of the working electrode,
the counter electrode having an extended portion physically separated from the electrolyte and extending away from the electrolyte in a second direction opposite to the first direction while maintaining a constant width of the counter electrode,
the reference electrode having an extended portion physically separated from the electrolyte and extending away from the electrolyte in the second direction while maintaining a constant width of the reference electrode,
an active surface area of the reference electrode being smaller than an active surface area of the working electrode and an active surface area of the counter electrode,
the working electrode, the counter electrode, and the reference electrode each comprising micro-perforated stainless steel, and
the working electrode further comprising a coating of nickel.

9. The method according to claim 8, the electrolyte being a proton exchange membrane (PEM).

10. The method according to claim 8, the device being placed in direct contact with a skin surface from which the sample is collected.

11. A device for measuring a concentration of a volatile anesthetic in a skin perspiration sample collected from a human subject, the device comprising:
a fuel cell based sensing device;
a means of displaying a concentration measured with the sensing device; and
circuitry configured to process and analyze concentration data output by the sensing device,
the sensing device comprising:
a sensor unit comprising a working electrode as an anode, a counter electrode as a cathode, a reference electrode, and an electrolyte;
circuitry configured to control a potential applied to the sensor unit; and
circuitry configured to measure a current output between the working electrode and the counter electrode and a potential between the working electrode and the reference electrode through the electrolyte,
the anode and the cathode being separated by, and in electrical contact with, the electrolyte, the working electrode being disposed on an anode side of the electrolyte, the counter electrode being disposed on a cathode side of the electrolyte opposite to the anode side of the electrolyte such that the counter electrode faces the working electrode, the reference electrode being disposed on the cathode side of the electrolyte, the reference electrode being in electrical contact with the electrolyte and disposed adjacent to, though separated from, the counter electrode, the working electrode, the counter electrode, and the reference electrode each comprising a thin coating of a material comprising iron, gold, platinum, carbon, or a combination thereof, as a catalyst, a thickness of the electrolyte being in a range of from 0.01 cm to 0.03 cm such that $H^+$ ions exchange between the working electrode and the reference electrode, a first part of the anode side of the electrolyte corresponding to the counter electrode being uncovered by the working electrode and a second part of the anode side of the electrolyte corresponding to the reference electrode being uncovered by the working electrode, the working electrode having an extended portion physically separated from the electrolyte and extending away from the electrolyte in a first direction while maintaining a constant width of the working electrode, the counter electrode having an extended portion physically separated from the electrolyte and extending away from the electrolyte in a second direction opposite to the first direction while maintaining a constant width of the counter electrode, the reference electrode having an extended portion physically separated from the electrolyte and extending away from the electrolyte in the second direction while maintaining a constant width of the reference electrode, an active surface area of the reference electrode being smaller than an active surface area of the working electrode and an active surface area of the counter electrode, the working electrode, the counter electrode, and the reference electrode each comprising micro-perforated stainless steel, and the working electrode further comprising a coating of nickel.

12. The device according to claim 11, further comprising an electronic platform coupled to the sensing device for receiving user input.

13. The device according to claim 11, further comprising a casing for enclosing the sensing device, the casing being adapted to a format selected from wearable accessories, apparels, shoes, and vehicular accessories.

14. The device according to claim 11, further comprising a power supply.

15. The device according to claim 11, the electrolyte being a proton exchange membrane (PEM).

* * * * *